United States Patent [19]

Farrar et al.

[11] Patent Number: 4,906,732

[45] Date of Patent: Mar. 6, 1990

[54] TREATMENT OF POLYACRYLAMIDE GEL PARTICLES WITH AMIDASE TO REDUCE RESIDUAL ACRYLAMIDE CONTENT THEREOF

[75] Inventors: David Farrar; Peter Flesher, both of West Yorkshire, Great Britain

[73] Assignee: Allied Colloids Limited, Great Britain

[21] Appl. No.: 308,832

[22] Filed: Feb. 9, 1989

[30] Foreign Application Priority Data

Feb. 10, 1988 [GB] United Kingdom ............... 8803064

[51] Int. Cl.$^4$ ................................................. C08J 9/04
[52] U.S. Cl. ..................................... 528/492; 528/491; 524/17; 524/500; 435/227; 435/228; 435/262
[58] Field of Search .................. 524/17, 500; 528/491, 528/492; 435/227, 228, 262

[56] References Cited

U.S. PATENT DOCUMENTS 4,687,807  8/1987  Wetegrove et al. ............... 524/827

FOREIGN PATENT DOCUMENTS 0272025  6/1988  European Pat. Off. ............ 435/228

*Primary Examiner*—Joseph L. Schofer
*Assistant Examiner*—F. M. Teskin
*Attorney, Agent, or Firm*—Ostrolenk, Faber, Gerb & Soffen

[57] ABSTRACT

A substantially dry, particulate polyacrylamide composition having reduced acrylamide monomer content is made by mixing amidase with coarse aqueous gel polymer particles, absorbing the amidase into the particles and subsequently drying the particles.

10 Claims, No Drawings

TREATMENT OF POLYACRYLAMIDE GEL PARTICLES WITH AMIDASE TO REDUCE RESIDUAL ACRYLAMIDE CONTENT THEREOF

This invention relates to the provision of polyacrylamides with reduced monomer impurity levels.

Polyacrylamides may contain small amounts of residual monomeric acrylamide and this is undesirable. It is known that acrylamide can be converted to acrylic acid by the action of an amidase. As an example, in JP-A-52045854 and JP-A-54041984 acrylamide is polymerised in the soil so as to stabilise the soil and contamination of the stabilised soil by free monomer is reduced by injecting amidase into the soil with the acrylamide that is to be polymerised. However this process is not very satisfactory since monomer can escape to the environment and monomer may be converted to acrylic acid before polymerisation, thus tending to form polyacrylic acid, and it is necessary for the operative to supply the enzyme as well as the polymerising solution.

Various other processes are known in which the user of the polymer reduces the residual acrylamide content in a preformed solution of polyacrylamide. Such processes are described in, for instance, JP-A-53086078, JP-A-53086079 and JP-5209447. For instance the latter includes an example in which 10g anionic polyacrylamide having a monomer concentration of 500ppm is diluted in water to 10 litres in the presence of enzyme solution, and the acrylamide monomer content is thus reduced. All these processes suffer from the disadvantage that the polymer solution must be made up first and the user, who has made up the solution, must than add the enzyme to it.

Polyacrylamide is generally supplied by the manufacturer to the user in the form of a powder or as a dispersion in water-immiscible liquid and it would be desirable for the manufacturer to be able to supply a material that, when diluted with water by the user, had a suitably low residual monomer content.

In U.S. Pat. No. 4,687,807 amidase is added to a water-in-oil emulsion of polyacrylamide which is then subjected to pH adjustment and/or heating and/or inert gas sparging and/or adding a chemical reducing agent. The overall process conditions, including this final step, are said to cause the amount of free acrylamide monomer in the aqueous emulsion to be reduced significantly.

It is stated in the patent that the amount of polymer in the emulsion may be from 5 to 60% and the amount of water from 20 to 90%. Thus the amount of water is always at least 33% by weight based on dry polymer.

In practice it is well known that water-in-oil emulsions do, in practice, always contain an amount of water within a much narrower range, and in particular the amount of water is generally within the range of 30 to 55% (which is stated in U.S. Pat. No. 4,687,807 as being the preferred amount of water). The presence of these significant amounts of water during the process are clearly essential to the process of U.S. Pat. No. 4,687,807 as the amidase would only effectively consume acrylamide monomer in an aqueous medium. The patent warns that if the emulsion is being heated then temperatures above 60° C. can be used only as long as deactivation does not become significant, and so this again indicates the criticality of maintaining the water in the emulsion.

We are particularly concerned with the production of substantially dry, particulate polyacrylamide compositions and with the desirability of ensuring that solutions made from such compositions have a very low acrylamide monomer content even if the initial polymer is contaminated with, for instance, 500 ppm or more, e.g., 1000 to 5000 ppm, acrylamide monomer (based on dry polymer). Accordingly none of the prior art on the incorporation of amidase into aqueous polyacrylamide compositions is of any relevance.

In Serial No. 07/308,836 filed even date herewith is described substantially dry compositions comprising a polyacrylamide and an amidase, the preferred compositions of that application having been made by mixing the amidase with substantially dry particles of the polyacrylamide.

The present invention relates to another way of producing substantially dry particles of polyacrylamide which have reduced amounts of inpurity monomer as a result of interaction with amidase.

According to the invention, a method of producing substantially dry particulate polyacrylamide having reduced acrylamide monomer content comprises mixing an amidase with aqueous gel particles that contain 20 to 50% by weight polymer and that have a dry size at least 50% by weight above 30$\mu$m, absorbing the amidase into the gel particles, maintaining the particles as aqueous gel for a sufficient period to allow reduction of the acrylamide monomer content, and drying the aqueous gel particles.

By this method it is possible to reduce the impurity monomer content in aqueous gel polymer whilst keeping it in aqueous gel form, and thereafter converting it in conventional manner to substantially dry particulate form wherein the polymer has a lower acrylamide content than it would have had if the amidase had not been mixed into it.

Generally at least 90% by weight of the particles are above 30$\mu$m, preferably above 50$\mu$m. Generally at least 90% by weight are below 2mm, preferably below 1mm, most preferably below 500$\mu$m. It is often preferred that at least 90% by weight are in the range 50 to 200$\mu$m. the dried particles generally have a water content of below 20%, and usually below 10% by weight.

It is surprising that useful results can be obtained by this technique since it would not have been expected that the useful effect of amidase would extend substantially throughout the gel particles. Bearing in mind the molecular size of the amidase, it would have been expected that any effect of it would have been restricted to, for instance, a surface layer 1 or 2 $\mu$m thick (comparable to the very small particle dimensions in U.S. Pat. No. 4,687,807). If this had occurred, then the process would not have achieved any useful reduction in acrylamide, but in fact a very useful reduction can occur and so clearly the effect of the amidase extends substantially throughout the gel particles, despite their large size.

The gel particles are generally the particles made by gel polymerisation in conventional manner and so have the conventional polymer content for this, generally 25 to 40%. The particles are generally formed during the process by gel polymerisation of ethylenically unsaturated monomer comprising acrylamide. The gel polymerisation may be by bulk polymerisation, in which event the particles are formed by comminuting the gel in conventional manner, or by reverse phase bead polymerisation in which event the particles may be formed as beads or by comminution of beads.

Although the process is defined as involving four stages, namely the mixing stage, the absorption stage, the maintenance stage and the drying, two or more of these stages may merge into one another. For instance some or all of the absorption stage may occur during the initial mixing, and some of the drying may be conducted during the maintenance stage. The overall process must, however, involve the polymer being maintained as aqueous gel in contact with absorbed amidase for sufficient period to achieve useful reduction of acrylamide monomer and conveniently therefore the process involves deliberately maintaining the particles for a significant maintenance period after the initial mixing and absorption is completed and before substantial drying occurs.

The maintenance period is generally at least 10 minutes, and usually at least 30 minutes or one hour. It can be as long as, for instance, ten hours but shorter periods, generally below five hours and preferably below three hours, are normally satisfactory. The absorption and maintenance temperatures must both be a temperature at which the amidase is substantially stable and is normally below 90° C., preferably below 70° C. Generally it is above 30° C., typically 30 to 50° C.

The mixing of the amidase with the coarse aqueous gel particles can be effected in air, for instance by spraying aqueous amidase on to the particles while they are being tumbled or otherwise agitated. The maintenance stage can be conducted while the particles are in air, for instance with occasional or continuous tumbling or other agitation. If the gel particles aggregate during the process, they may be comminuted in conventional manner.

In another process the coarse gel particles are contacted with the amidase while they are suspended in an aqueous medium in which they do not substantially swell or dissolve. It may contain one or more agents to prevent substantial swelling or dissolution of the particles, for instance as described in EP 169674. Preferably a polymeric agent is used, as described in EP 169674. When the contact is effected in an aqueous medium, the particles can be comminuted to the desired size and then dispersed into the medium or they can be milled to the desired size in the medium. The amidase can be added to a previously formed dispersion of the particles in the aqueous medium or it can be present in the medium initially, for instance before milling the particles in the medium. The polymer particles will be maintained in the aqueous medium containing the amidase for the desired digestion period and may then be separated, e.g., by filtration such as centrifugation, and dried by fluid bed drying or other conventional drying techniques. They may be further comminuted.

These methods (involving mixing and maintenance either in air or in an aqueous medium) are often preferred but in another method, the coarse aqueous gel particles are contacted with the amidase while dispersed in an organic liquid. The coarse gel particles may have been made by reverse phase bead polymerisation or by bulk gel polymerisation followed by comminution. Any comminution may have been effected on the gel before it was dispersed in the organic liquid or it may be milled to the desired size in the liquid, and the amidase may be introduced after the polymer or may be present in the liquid before the polymer is incorporated into it.

In one method of this type, the organic liquid is methanol or other polar, water miscible, liquid. In another method of this type, the organic liquid is a water immiscible liquid, for instance a hydrocarbon, typically a hydrocarbon of the type conventionally used for reverse phase polymerisation. The amount of organic liquid is generally from 0.5 to 5, preferably 1 to 3 and often about 2 parts organic liquid per part aqueous gel, so that the dry polymer content in the organic liquid is often in the range 5 to 20%, often 10 to 15% by weight of the total composition.

A preferred process comprises forming the gel particles in the water immiscible liquid by reverse phase bead polymerisation in conventional manner, adding the amidase, maintaining the mixture at the chosen temperature for, e.g., 10 minutes to 5 hours, azeotroping the system to dry the beads, and separating them and further drying in air if necessary in conventional manner.

When the amidase is to be added to water immiscible liquid, it can sometimes be convenient to introduce the amidase in the form of an aqueous emulsion in an oil that is miscible with the water immiscible liquid. After maintaining the polymer in the organic liquid for the desired maintenance period it may then be separated from the organic liquid and dried in conventional manner. For instance the organic liquid may consists of or include organic liquid that forms an azeotrope with water and the polymer gel may be dried by azeotroping the mixture followed by centrifuging or other filtration, optionally followed by further drying, in conventional manner. The particles may be further comminuted.

The amount of particulate or aqueous amidase will be selected according to the concentration of amidase, the activity of the amidase and the amount of monomer. Suitable amounts that are effective for achieving the desired reduction can easily be found by routine optimisation. Typically the amount is 0.05 to 5%, often 0.1 to 1%, dry weight enzyme based on dry weight polymer.

The drying stage may have deactivated the amidase but, especially if the drying is conducted at relatively low temperatures, the dry particulate composition may include amidase, as described in application Ser. No. 07/308,836 filed even date herewith. In this event, further reduction in acrylamide monomer may occur when the dry particulate composition is dispersed into water, for instance for two hours at 25° C.

The amount of amidase and the materials that are used is preferably such that the resultant content of acrylamide monomer is below 1000 ppm, often below 500 ppm and preferably below 100 ppm, based on dry polymer. Values of below 50 ppm and even below 5 ppm can be obtained in the invention. In particular, when the particles are dispersed into water for two hours at 25° C. the resultant solution may have a monomer content (based on the weight of polymer) within these ranges.

The polyacrylamide that is treated in the invention can be a homopolymer of acrylamide or it can be a copolymer with one or more ethylenically unsaturated non-ionic, anionic or cationic monomers. The amount of comonomer can be from 1 to 99% by weight but is usually below 90% and often below 70% by weight. Typical non-ionic monomers include styrene and N-vinyl pyrollidone. Typical anionic monomers are ethylenically unsaturated carboxylic and sulphonic monomers, especially (meth) acrylic acid and 2-acrylamido-2-methyl propane sulphonic acid. Typical cationic monomers are diallyl dimethyl ammonium chloride and dialkylaminoalkyl (meth) -acrylates and -acrylamides, generally as acid addition or quaternary ammonium salts.

The polymer can be water soluble or water insoluble but swellable, for instance as a result of cross linking e.g., by copolymerisation with poly-ethylenically unsaturated cross linking agent in known manner.

The polymer may be polymerised to any convenient molecular weight at which it can form powdered particles. Accordingly the molecular weight will usually be above about 100,000 and often above 500,000. Values in the range 1 to 30 million or higher often being preferred.

The content of monomer in the initial polymer can be quite low, e.g., 300 ppm, but often it is above 500 ppm and frequently above 1000 ppm (based on the dry weight of polymer). It is usually below 5000 ppm but can be higher. The process of the invention typically reduces monomer content by at least one third, preferably at least two thirds and most preferably by at least three quarters of initial monomer content.

Prior to the invention it has been necessary to select initiator and polymerisation conditions so as to minimise residual monomer and an inevitable consequence has been that molecular weight is depressed. As a result of the invention the polymerisation can be conducted to give maximum molecular weight and the resultant high level of residual monomer can then be reduced by teh process of the invention.

Any of the amidase that are known for converting acrylamide to acrylic acid can be used, including any of those mentioned in the literature quoted above. Particularly preferred are Brevibacterium ammoniagenes especially those described in JP-A-53086078. Preferably the seed strain of B. ammoniagenes is cultured at 25°–35° C. and pH 6.5–8.5 in a liquid culture medium containing carbon source, nitrogen source, inorganic salts and other nutrients. After cultivation the bacterial body is separated by filtration and the crude enzyme can be obtained by drying the bacterial body by acetone or by freeze drying and breaking the bacterial cells by mashing in buffer solution or subjecting to supersonic waves. Preferred species are ATCC 1641, ATCC 6871 and ATCC 6872. Other suitable amidases are those described in JP-A-53086079. These include the intracellular enzyme of Brevibacterium acetylicum, B. helvorum, B. lucinophagum, B. linens or B. vitarumen. They may be cultured in the similar manner. Preferred materials are B. acetylicum ATCC 953, B. helvolum ATCC 11822, B. lucinophagum ATCC 13809, B. linens ATCC 8377 and B. vitarumen ATCC 10234.

Other suitable enzymes are mixtures of Bacillus and Pseudomonas, e.g., Bacillus sphaericus IAM 1286 and Pseudomonas putrefaciens ATCC 8071 or mixtures of Brevibacterium (except for B. ammoniagenes) and Pseudomonas, e.g., B. acetylicum ATCC 953 and P. putrefaciens ATCC 8071 or mixtures of Brevibacterium and Bacillus, e.g., Bacillus brevis IAM 1031 and Brevibacterium ammoniagenes IAM 1641, as described in, respectively, JP-A-52099281, JP-A-5294473 and JP-A-52094470.

It will be appreciated that the amidase may be pure or semi-pure or may be bacterial cells or any other fraction having the desired enzyme activity for converting acrylamide. Cofactors and other materials that promote enzymatic activity may be included in the aqueous gel with the enzyme.

The following are some examples.

EXAMPLE 1

An anionic flocculant copolymer of acrylamide and acrylic acid is produced by conventional bulk solution polymerisation techniques to yield a gel of 34% solids in water, with a polymer of 50 wt % anionic character. The gel is processed using a domestic meat mixing machine to yield wet gel chips of 0.5–5mm in diameter.

200g of the gel is placed in the bowl of a domestic food processor and agitated by the action of the rotating blades. Amidase as a concentrated aqueous solution is added to the mix and coats the gel surfaces. The treated gel is then hot air dried after a 60 minute holding period to allow diffusion of the agent. The dry gel chip is ground and sieved to 850–150μm. The product polymer chip of 94% dry weight exhibits good solubility in water yielding lump free solutions. The copolymer had an intrinsic viscosity of 18 in 1M NaCl at pH 7 and 25° C. The product contains 0.04% free acrylamide.

EXAMPLE 2

A high molecular weight polyacrylamide is prepared by conventional bulk solution polymerisation techniques to yield 300g of gel polymer at 28% polymer solids. The gel is comminuted to yield wet gel chips of 0.5mm–5mm in diameter.

The gel particles are added steadily to 600 g of a 40% active poly(sodium acrylate) solution (Mw 1000–10,000) while the mix is subjected to mixing using a Silverson Laboratory Mixer equipped with a 2mm square hole high shear screen.

Once all the gel has been processed to yield a finely chopped gel suspension the required quantity of amidase is introduced to the stirred suspension. After sufficient reaction time the gel is collected and fluid-bed dried before grinding and sieving. The product polymer of 92% dry weight is of intrinsic viscosity 17 and has a residual free acrylamide level of 0.04%.

EXAMPLE 3

Polyacrylamide gel prepared as example 2 is added to 450g of a hydrocarbon oil (Isopar G of Essochem) while subjected to Silverson cutting.

The cut suspension is treated with a solution of amidase in water (25g) and allowed to diffuse and react. The gel is separated from the hydrocarbon solvent dried and ground to yield particles of 850–150μm.

EXAMPLE 4

A 75:25 by weight acrylamide:sodium acrylate gel copolymer is prepared by bulk gel polymerisation of 100 parts of a 30% by weight aqueous monomer solution in conventional manner. The resultant hot gel is allowed to cool. It is cut into strands and then comminuted into gel particles having dimensions generally in the range 5 to 10mm.

These particles are sprayed with 40 parts by weight of a water-in-oil emulsion containing 20 parts of an aqueous amidase preparation emulsified into 80 parts of a hydrocarbon solvent having flash point 41° C. and containing 0.4 parts sorbitan mono oleate emulsifier. The aqueous amidase preparation has a concentration of 4 units/ml at 30° C., where 1 unit is defined as 1 micromole of acrylic acid produced per minute at 30° C.

The treated gel slurry is gently agitated for 5 minutes and excess solvent then removed by decantation. The treated gel particles are stored in a capped bottle at 20° C. for 24 hours.

A small portion of the untreated gel is assayed for residual free acrylamide by extraction into 70% aqueous methanol and GLC analysis. Similarly, portions of the treated gel are assayed after 2 hours maintenance period in the bottle and after the full 24 hours. It is found that the free acrylamide level drops from 2100 ppm in the untreated sample to about 500 ppm in 2 hours and to less than 50 ppm after 24 hours.

We claim:

1. A method of producing substantially dry particulate polymer of acrylamide having reduced acrylamide monomer content and comprising mixing amidase with aqueous gel particles that contain 20 to 50% polyacrylamide or acrylamideethylenically unsaturated monomer copolymer and that have a dry size at least 50% by weight above 30 $\mu$m, absorbing the amidase into the gel particles, maintaining the particles as aqueous gel for a sufficient period to allow reduction of the acrylamide monomer content, and drying the aqueous gel particles.

2. A method according to claim 1 in which, after mixing the amidase with the gel particles, the particles are maintained at 30 to 70° C. for from 10 minutes to 5 hours before the drying.

3. A method according to claim 1 in which the particles have a size of at least 90% by weight between 50$\mu$m and 2 mm.

4. A method according to claim 1 in which the mixing is effected by mixing an aqueous amidase composition with the aqueous gel particles.

5. A method according to claim 1 in which the aqueous gel particles are in air during the said mixing and said maintaining stages.

6. A method according to claim 1 in which the aqueous gel particles are suspended in an aqueous medium in which they do not substantially swell or dissolve during the said mixing and said maintaining stages.

7. A method according to claim 1 in which the gel particles are dispersed in an organic liquid during the said mixing and the said maintaining stages.

8. A method according to claim 7 in which the organic liquid is a water immiscible liquid and the particles are formed in it by reverse phase bead polymerisation and the drying is effected by azeotroping and the particles are then separated from the liquid.

9. A method according to claim 1 in which the dry particles have an acrylamide monomer content of below 1,000 parts monomer per million parts polymer of acrylamide.

10. A method according to claim 1 in which the dry particles have an acrylamide monomer content of below 100 parts monomer per million parts polymer of acrylamide.

* * * * *